United States Patent [19]

Baust et al.

[11] Patent Number: 5,437,673
[45] Date of Patent: Aug. 1, 1995

[54] CLOSED CIRCULATION TISSUE WARMING APPARATUS AND METHOD OF USING THE SAME IN PROSTATE SURGERY

[75] Inventors: John G. Baust, Candor; Zhao H. Chang, Binghamton, both of N.Y.; Jeffrey Cohen, Pittsburgh, Pa.; Gary Onik, Allison Park, Pa.; George Reyes, Pittsburgh, Pa.

[73] Assignee: Cryomedical Sciences, Inc., Rockville, Md.

[21] Appl. No.: 13,307

[22] Filed: Feb. 4, 1993

[51] Int. Cl.[6] ................................. A61M 25/00
[52] U.S. Cl. .................................. 606/23; 604/30
[58] Field of Search .............. 604/96, 113; 606/23, 606/108, 191, 280, 264, 24

[56] References Cited

U.S. PATENT DOCUMENTS

| | | |
|---|---|---|
| 2,058,780 | 10/1936 | Elliott . |
| 2,077,453 | 4/1937 | Albright . |
| 3,087,493 | 4/1963 | Schossow . |
| 3,125,096 | 3/1964 | Antiles et al. . |
| 3,425,419 | 2/1969 | Dato . |
| 4,345,598 | 8/1982 | Zobac et al. ................. 606/24 |
| 4,377,168 | 3/1983 | Kzasa et al. .................. 606/24 |
| 4,571,240 | 2/1986 | Samson et al. . |
| 4,597,755 | 7/1986 | Samson et al. . |
| 4,844,074 | 7/1989 | Kurucz . |
| 4,946,460 | 8/1990 | Merry et al. ................. 606/24 |
| 4,955,895 | 9/1990 | Sugiyama et al. . |
| 4,994,066 | 2/1991 | Voss ............................. 606/108 |
| 5,047,045 | 9/1991 | Arney et al. . |
| 5,053,004 | 10/1991 | Markel et al. . |
| 5,139,496 | 8/1992 | Hed .............................. 606/24 |
| 5,147,355 | 9/1992 | Friedman et al. ........... 606/23 |
| 5,207,674 | 5/1993 | Hamilton ..................... 606/23 |
| 5,254,116 | 10/1993 | Baust et al. .................. 606/23 |
| 5,257,977 | 11/1993 | Eshel ............................ 604/96 |
| 5,269,802 | 12/1993 | Garber ......................... 606/191 |
| 5,275,595 | 1/1994 | Dobak, III ................... 606/24 |

*Primary Examiner*—C. Fred Rosenbaum
*Assistant Examiner*—Manuel Mendez
*Attorney, Agent, or Firm*—Sherman and Shalloway

[57] ABSTRACT

The present invention is directed to a closed circulation tissue warming apparatus for use during surgery to maintain the temperature of tissues at a desired level and to a method of using the apparatus in prostate surgery particularly during transperineal cryoablation of the prostate gland in human males to maintain the temperature of the urethral tissues and thereby prevent urethral sloughing. It may also have utility where it is desired to lower the temperature of surrounding tissues, such as during laser ablation. The apparatus includes a multilumen catheter inserted into the urethra and connected to a fluid warming and circulation control means whereby warmed water is circulated through the lumens at a controlled flow rate and temperature. The concentric lumen structure of the catheter provides improved flow and even temperature maintenance along the length of the catheter and the urethra.

6 Claims, 5 Drawing Sheets

CLOSED CIRCULATION TISSUE WARMING APPARATUS AND METHOD OF USING THE SAME IN PROSTATE SURGERY

BACKGROUND OF INVENTION

The present invention is directed to a closed circulation tissue warming apparatus for use during surgery to maintain the temperature of tissues at a desired level and to a method of using the apparatus in prostate surgery. The apparatus is particularly useful in cryosurgery to prevent damage to tissues surrounding a surgical site from the extremely cold temperatures employed therein. The apparatus is especially useful during transperineal cryoablation of the prostate gland in human males to maintain the temperature of the urethral tissues and thereby prevent urethral sloughing. The apparatus may also have utility where it is desired to lower the temperature of surrounding tissues, such as during laser ablation.

Temperature variation of body tissues by irrigation with or circulation of thermal fluids is known as shown by patents to Elliott, U.S. Pat. No. 2,058,780, Albright, U.S. Pat. No. 2,077,453, Antiles, et al., U.S. Pat. No. 3,125,096, Dato, U.S. Pat. No. 3,425,419, and Kurucz, U.S. Pat. No. 4,844,074. However, these prior patents do not suggest either the specific structure of the apparatus of the present invention or the advantages obtained therewith in terms of control, ease of use, uniformity of fluid flow and temperature, and utility in cryoablation surgery of the prostate.

Elliott, U.S. Pat. No. 2,058,780, discloses a thermo therapeutical method and apparatus for treatment of body cavities, such as the vagina, rectal applications for treatment of the prostate gland, and the like. In this apparatus a distensible bag of conductive material is inserted into the body cavity and water or other fluid at a moderate temperature is introduced under sufficient pressure to cause distension of the bag. The Water circulates through the bag and its temperature is gradually elevated to the level desired for effective treatment of the area. Elliott discloses the thermal application using this apparatus and method to be useful in destruction of pathogenic bacteria without destroying the tissues being treated. There is nothing to suggest such a closed circulation of fluid in conjunction with cryosurgery to prevent damage to surrounding tissues. Furthermore, the structure of Elliott's, i.e. a simple bag, does not provide a uniform flow of fluid through the system for even temperature maintenance, rather, flow through Elliott's device will tend to be turbulent. However, the present system, by employing a catheter wherein the fluid path is through concentric lumens, achieves a more uniform flow and more even temperature throughout its length. With regard to prostate treatment, the Elliott device discloses direct application of heat to the prostate using the patented device whereas the present system is principally for use in combination with cryogenic surgery of the prostate to prevent damage to the surrounding tissues of the urethra.

Albright discloses a therapeutical appliance in the form of applicators adapted for insertion into various natural body cavities for application of heat by circulating hot water through the applicator. The structure of the applicator comprises a relatively long tube of thin elastic rubber having a central integral rubber web dividing the tube into two parallel channels joined at the tip. Such a structure is not suggestive of the apparatus of the present invention which provides improved flow of the circulating fluid, a more even application of thermal treatment to tissues and simultaneous drainage of the cavity being treated through a structure comprising concentric lumens.

Antiles, et al., U.S. Pat. No. 3,125,096, presents a body cooling apparatus whereby a refrigerant can be delivered to and evaporated within the body to effect cooling thereof. The structure of the apparatus used, while comprising multiple lumens within an esophageal tube is principally that of a balloon catheter with the balloon forming the refrigeration chamber. The lumens within the esophageal tube are separate and independent and comprise refrigerant introduction and removal tubes, a pressure monitoring tube and a stomach evacuation tube and are not concentric. Furthermore, there is no suggestion of use of such a device in the urethra in the manner of the present invention.

Dato, U.S. Pat. No. 3,425,419, discloses a method of lowering and raising the temperature of the human body by use of a thermal exchange catheter inserted within the flowing blood stream of the body. The catheter employed is an elongated tubular device of stainless steel and comprises, in one form, an inner tube and a concentric outer tube which communicate at the tip. Inasmuch as this device is designed for use in the blood stream, there is no provision for drainage of the body while the device is in use. Nor is there any suggestion of use in combination with cryogenic means for controlling the temperature of tissues around a cryogenic surgery site.

Kurucz, U.S. Pat. No. 4,844,074, discloses a method and apparatus for introducing a fluid into a human or animal organism and a method and heating device for temperature control. The apparatus and method are particularly directed to use in peritoneal dialysis and relate to the introduction of a physiological fluid at a prescribed temperature where the fluid is pumped through a controlled heating device into a gravity tank from where it is delivered to the body by gravity flow through the heating device a second time. This patent is particularly directed to the structure and function of the heating means and contains no disclosure relating to control of tissue temperatures around a cryogenic surgical site. Nor is there any disclosure relating to structure of an apparatus providing a means for closed circulation of the heated fluid within a body cavity while providing for simultaneous drainage of that cavity. In fact, it is not at all evident from the patent that the Kurucz system is, or is intended to be, a closed circulation system.

Similarly, concentric lumen and balloon catheters are also known such as devices disclosed by Schossow, U.S. Pat. No. 3,087,493; Samson, et al., U.S. Pat. No. 4,571,240; Samson, et al., U.S. Pat. No. 4,597,755; Sugiyama, et al., U.S. Pat. No. 4,955,895; Markel, et al., U.S. Pat. No. 5,053,004; and Arney, et al., U.S. Pat. No. 5,047,045. However, none of them suggest the structure of the present catheter nor the advantages obtained thereby in terms of uniform flow and temperature maintenance. Furthermore, there is no suggestion of use of this type of catheter in a method of cryoablative prostate surgery.

Devices currently on the market that the inventor is aware of and which bear the closest resemblance to the apparatus described herein are a urethral dilation balloon catheter manufactured by Cook Urological and the Level 1 Fluid IR-600 Normothermic Irrigation Set manufactured by Level 1 Technology. However, these devices do not include the structure of the present device nor do they provide a closed circulation system with the attendent advantages therein.

The Cook device is limited to a balloon dilation catheter wherein a latex balloon is expanded by filling it with air for the specific purpose of dilating the urethra. No provision is made for circulation of a warming fluid in either an open system or a closed system. Neither does this device suggest the catheter structure of the present invention wherein concentric lumens allow for counter current flow of a warming fluid for even temperature maintenance along the urethra.

The Level 1 Northermic Irrigation Set does provide a means for maintaining urethral temperature. However, this is not a closed circulation system, rather it is an open irrigation system that uses warmed water to prevent hypothermia in a patient. This device employs a standard Foley catheter for delivery of warmed irrigating liquid into the patient and does not provide any means whereby that liquid may be returned to a reservoir for recirculation. In this sense it is more in the nature of a lavage system. Furthermore, fluid pressure is maintained solely by gravity flow and, therefore, cannot provide the regulation of constant and even tissue warming and the maintenance of tissue temperature that the powered system of the present invention provides.

Accordingly, the Cook and Level 1 devices neither disclose nor suggest the apparatus of the present invention and its method of use.

SUMMARY OF INVENTION

It is an object of this invention to provide a closed circulation tissue warming apparatus which allows circulation of a warming fluid therethrough in an efficient manner while simultaneously providing drainage of the body cavity in which it is inserted.

It is a further object of this invention to provide an apparatus which is constructed to facilitate fluid circulation therethrough and optimum thermal transfer between the circulating fluid and surrounding tissues.

It is a still further object to provide an apparatus which is particularly suitable for use in combination with a cryogenic probe for cryoablation of tumors to protect surrounding tissues from extreme cold.

It is an even further object to provide a method for transperineal cryoablation of the prostate gland wherein the apparatus is used to maintain the temperature of urethral tissues.

Further objects and advantages will become evident from the following description and the drawings presented herein.

The present invention is directed to a closed circulation tissue warming apparatus and method of use wherein heated fluid is circulated through a multi-lumen catheter inserted in a natural body orifice to maintain the surrounding tissues at a temperature sufficient to prevent damage by cryogenic means used in the area and finds particular utility in the maintenance of urethral tissue temperatures during cryosurgery of the prostate gland. The apparatus comprises a multi-lumen catheter and an associated system for holding, heating and circulating a sterile fluid and which includes control means to regulate the temperature and flow rate of the fluid at desired values.

The principal portion of the apparatus is the multilumen catheter which is particularly designed for insertion into the urethra of a patient undergoing cryoablative prostatectomy. In this respect the catheter comprises an elongated urethral catheter having a central drainage lumen and about which are disposed spaced, concentric sleeves of thin plastic forming inflow and outflow lumens which are in fluid communication at the distal end of the device, the outer sleeve extending beyond the end of the inner sleeve and being sealed to the body of the urethral catheter. The proximal ends of the sleeves are connected to inflow and outflow blocks which provide fluid connection of the inflow and outflow lumens to fluid conduits which, in turn, connect to a reservoir of sterile fluid. In this manner a closed loop circulation system from the reservoir through the conduits and lumens and back to the reservoir is provided. The apparatus also includes heating and pumping means for heating and circulating the fluid and control means whereby temperatures and flow rates may be maintained in response to signals provided by sensors monitoring the fluid. The heater, pump and control means are reusable whereas the catheter, reservoir and connecting conduits are disposable.

In the preferred method of use of the apparatus, the catheter is inserted through the patient's urethra to the bladder and is connected to the reservoir by conduits at the inflow and outflow blocks. The central drainage lumen of the urethral catheter provides drainage of the bladder while the device is in place to avoid build up of pressure within the bladder. Following insertion of the catheter, the system is activated to begin heating and circulation of the fluid and the desired temperature and flow rate are selected, the control means serving to maintain these settings. Inflow and outflow temperatures of the fluid are monitored and any deviations from the desired temperature are detected and corrected by the control means. The concentric nature of the inflow and outflow lumens along the catheter provide both a uniform, relatively non-turbulent, flow of fluid through the device as well as an even temperature along the length of the catheter and the urethra. Since the inflow lumen is within the outflow lumen, the slightly warmer incoming fluid transfers heat to the outgoing fluid in the outflow lumen thereby providing a more even temperature range along the urethra.

The apparatus may find additional utility in other areas of surgery where thermal treatment of maintenance of tissues is required with or without the capability of drainage. For example, an extended length catheter may be used for thermal treatment within the intestinal tract or the esophagus. Shorter versions may find utility in other areas such as nasal passages, otic areas, joints i.e. arthroscopy, or the like, where adjacent tissues may be undergoing cryogenic or other thermal treatment. Indeed, varied forms of the apparatus and method may be used in virtually any body cavity where tissues are exposed to thermal extremes and damage to adjacent tissues is to be avoided. They may find particular utility anywhere cryogenic probe devices are being used to destroy and/or remove tumerous growths. Furthermore, the apparatus and method are readily adaptable to use in cooling of body tissues by substituting a cooling fluid for the circulating heating fluid. The only limitation to this variety of uses is that the apparatus be constructed to a size and have a fluid capacity appropriate to the patient and/or area of the body in which it is being used.

DETAILED DESCRIPTION OF THE PREFERRED EMBODIMENT

The following description is based on the preferred embodiment of the invention as a warming system for use in combination with cryogenic means for prostate surgery in human male patients. As such any dimensions, volumes and the like are based on such use and the physiology of an average adult human male. However, the invention is by no means limited to such use and size and the apparatus may be made smaller or larger both in length and diameter depending on the intended location of use, the age, or the size of the patient on which it is used. In fact, although the description herein is directed to urethral use, it is considered to be within the scope of this invention to include utility elsewhere in the body and in different ages, sizes and sexes of patients. Accordingly, the stated dimensions and volumes are considered to be merely exemplary since they may change depending on the ultimate use of the apparatus.

Figure 1:
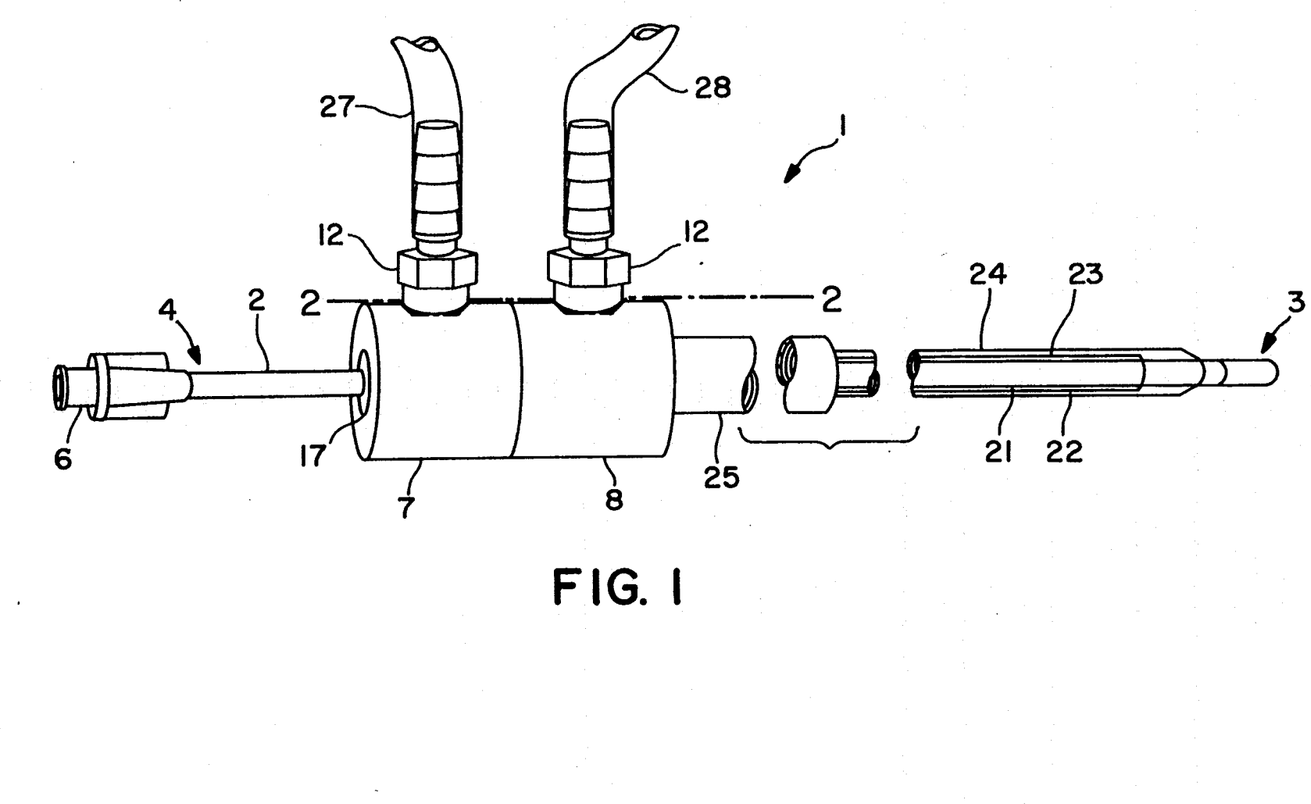
FIG. 1 is an oblique view of a multi-lumen catheter of the tissue warming system of the present invention.
Figure 2:
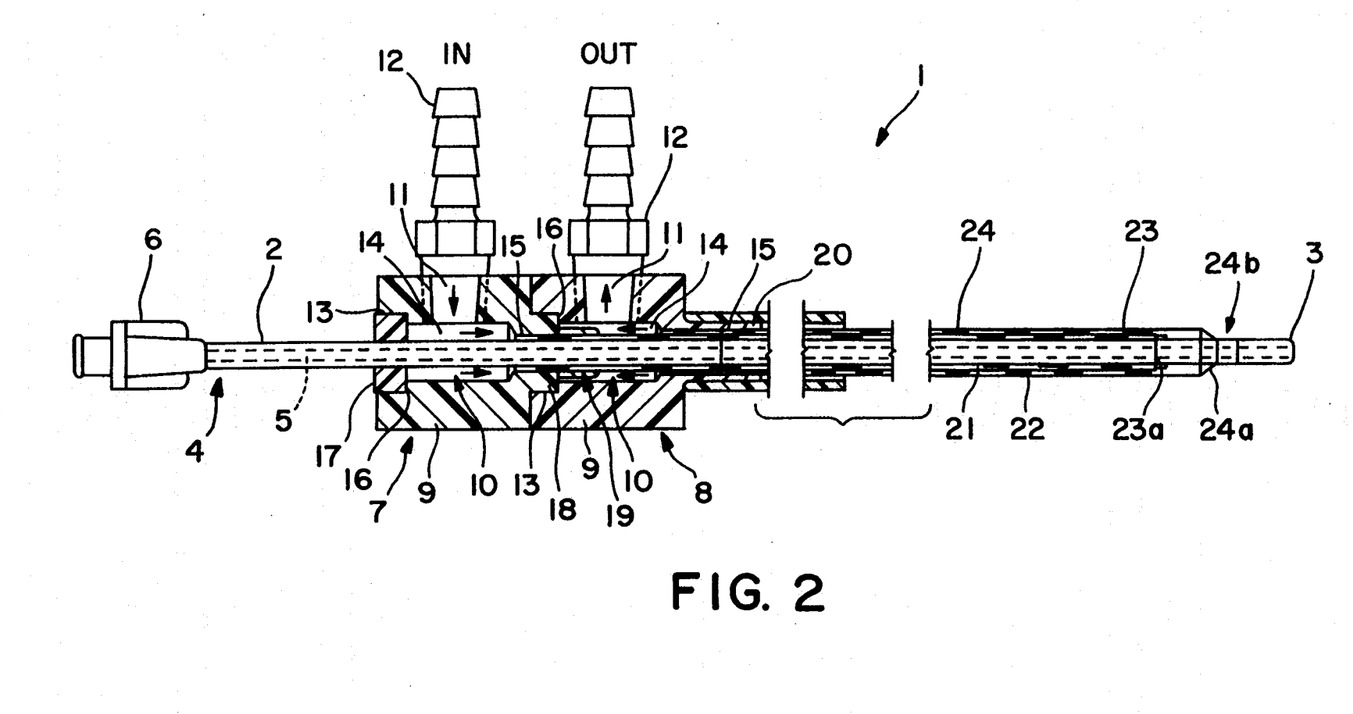
FIG. 2 is a longitudinal partial cross section along line 2—2 of the multi-lumen catheter of FIG. 1.

FIGS. 1 and 2 illustrate multi-lumen catheter 1 which is the principal part of the system of the present invention. Multi-lumen catheter 1 is built around stiff hollow shaft 2 in the form of an elongate catheter which has distal end 3, proximal end 4 and central drainage lumen 5. Preferably, shaft 2 is a standard urethral catheter having a length of 30 to 40 centimeters and a preferred diameter of 15 French, although other diameters may be used. Shaft 2 is also preferably made from polyurethane and has a connective fitting 6 at proximal end 4.

Positioned adjacent to proximal end 4 and concentric to shaft 2 are inflow and outflow blocks 7 and 8. Preferably, inflow block 7 is proximal to outflow block 8, the blocks being interfitting as will be hereafter explained. Blocks 7 and 8 are substantially identical and comprise a substantially cylindrical body 9 having a central longitudinal bore 10, a transverse fluid port 11 and a tube fitting 12. Longitudinal bore 10 is divided into three sections, a proximal countersink 13, a main chamber 14 of slightly smaller diameter than countersink 13 and an outlet passage 15 of still smaller diameter. Each section is larger in diameter than shaft 2 which passes through bore 10 of both inflow block 7 and outflow block 8 and the respective transverse fluid ports 11 communicate with main chamber 14 of each block.

In the case of inflow block 7, countersink 13 provides a shoulder 16 against which plug 17 fits to seal the proximal end of bore 10 around shaft 2. The distal end of inflow block 7 is formed with a cylindrical plug 18 in axial alignment with bore 10 to fit in the corresponding countersink 13 of outflow block 8. Cylindrical plug 18 of inflow block 7 fits against shoulder 16 of outflow block 8 to close chamber 14 therein and prevent leakage between blocks 7 and 8. A cylindrical extension 19 projecting axially from the end of plug 18 projects part way into chamber 14 of outflow block 8. A similar cylindrical extension 20 is provided on the distal end of outflow block 8 and is of slightly larger inside diameter than cylindrical extension 19. The purpose of extensions 19 and 20 will be explained presently. At this time it is noted that the respective chambers 14 of inflow and outflow blocks 7 and 8 have diameters sufficient to allow free flow of fluid therein around shaft 2. In addition, all connections between blocks 7 and 8 and shaft 2 are fluid tight to prevent leakage.

Inflow and outflow blocks 7 and 8 provide fluid access to concentric lumens 21 and 22 along the length of shaft 2 distally of blocks 7 and 8. Lumens 21 and 22 provide a closed fluid circulation path along the length of catheter 1 from inflow block 7 to outflow block 8 and are defined by shaft 2, concentric inner sleeve 23 and concentric outer sleeve 24. Sleeves 23 and 24 are preferably made from a flexible, relatively non-stretchable, polyester film such as polyethylene terephthalate, outer sleeve 24 having a fixed diameter upon introduction of fluid into lumen 22. Preferably, this diameter is about 22 French, which corresponds to the average diameter of the urethra in adult male humans. The proximal end of inner sleeve 23 connects to cylindrical extension 19 to form a fluid tight seal with inflow block 7 and extends bore 10 of block 7 through outflow block 8 and along shaft 2 as lumen 21, the inside diameter of sleeve 23 being the same as the inside diameter of extension 19. Similarly, the proximal end of outer sleeve 24 connects to cylindrical extension 20 of outflow block 8 to form a fluid tight seal therewith and extend bore 10 of block 8 along shaft 2 as lumen 22. In order to form a closed loop fluid path and thereby provide a fluid return from inner lumen 21 through outer lumen 22, the distal end 24a of outer sleeve 24 is reduced and sealed at 24b to shaft 2 adjacent the distal end thereof, preferably approximately 1 centimeter from the distal end 3. Inner sleeve 23 terminates at 23a a short distance proximally of the sealed distal end of outer sleeve 24, approximately 5 mm proximally, and is left open within the distal end of outer sleeve 24 so that fluid introduced into inner lumen 21 through inflow block 7 may pass out of inner lumen 21 into outer lumen 22 and return the length of catheter 1 to outflow block 8. This concentric structure allows for a uniform flow of fluid in both directions (as shown by arrows in FIG. 2) along the length of catheter 1 as well as providing a more uniform temperature along the length of the urethra in which catheter 1 is inserted. The countercurrent flow of incoming and outgoing fluid allows the warmer incoming fluid in inner lumen 21 to warm the cooler outgoing fluid in outer lumen 22. The thermal exchange is more even along the length of catheter 1 and encompasses the entire circumference thus producing a more uniform temperature along the length of the urethra. As protection against damage due to excessive flexing, a strain relief 25 in the form of a length of heavier gauge plastic tubing is attached to the distal face of outflow block 8 by telescoping a portion of the tubing over the outer surface of cylindrical extension 20. Strain relief 25 extends a distance of approximately five centimeters beyond the end of cylindrical extension 20.

Once again it is noted that the entire apparatus of the multi-lumen catheter 1 may be constructed in larger or smaller sizes as needed depending on the criteria of patient and use as previously noted. For example, a multi-lumen catheter 1 for use on a child will be smaller than that used on an adult. Similarly, a multi-lumen catheter 1 for use elsewhere in the body may be smaller or larger than that used in the urethra.

Figure 3:
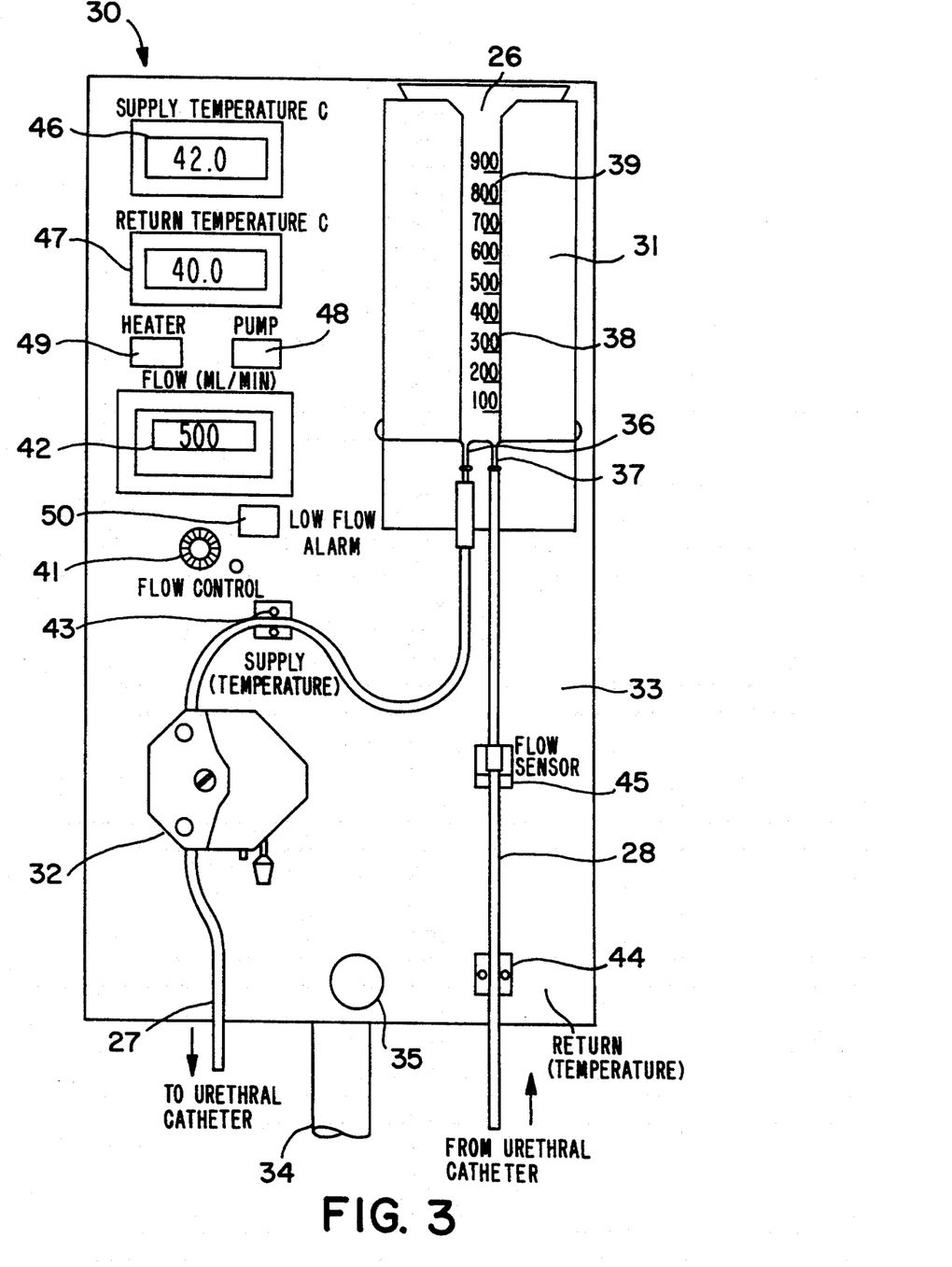
FIG. 3 is a planar front view of a heater and pump unit of the tissue warming system of the present invention.
Figure 4:
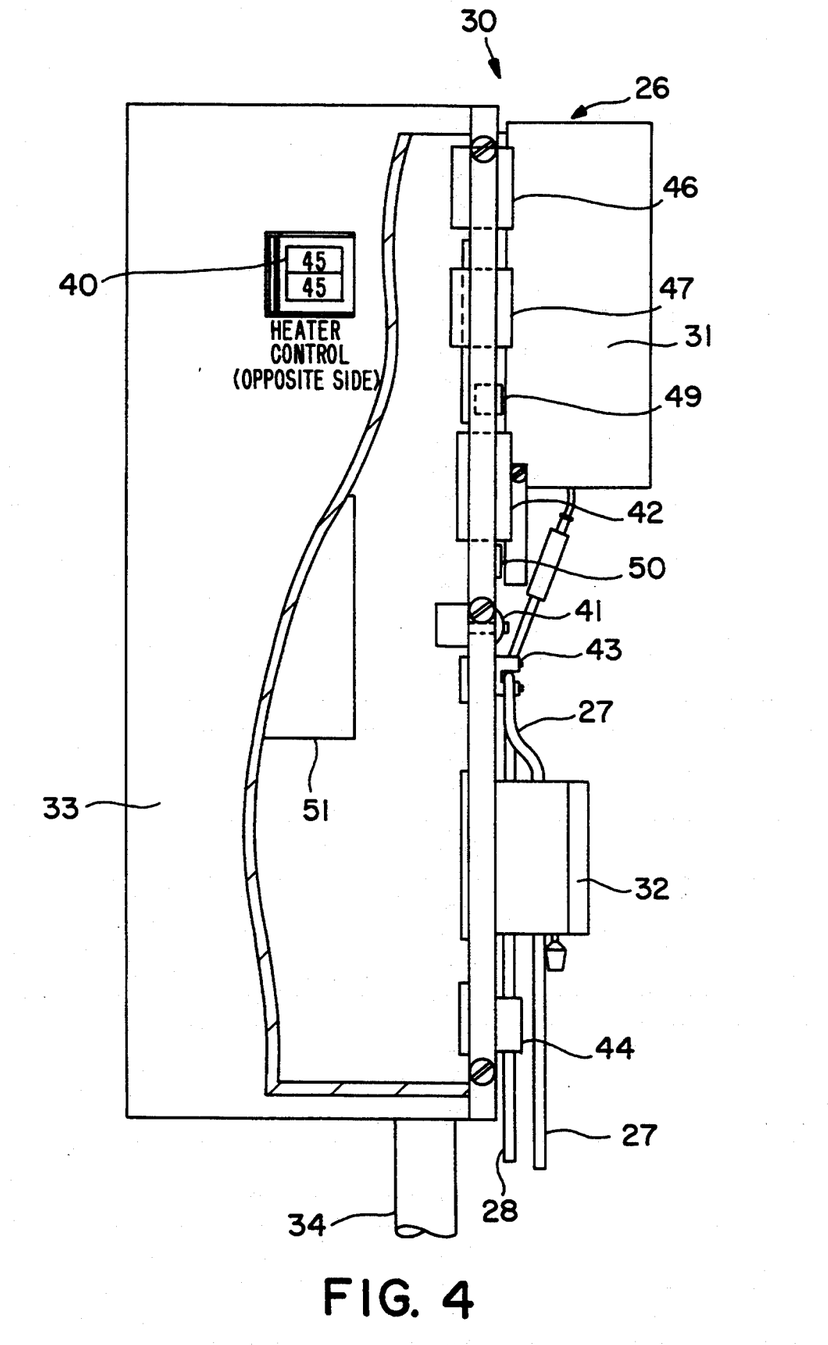
FIG. 4 is a partial cut-away side view of the heater and pump unit of FIG. 3 illustrating the arrangement of control elements therein.

Turning now to FIGS. 3 and 4, fluid reservoir 26 and conduits 27 and 28 together with control apparatus 30 for the system are illustrated. Control apparatus 30 comprises heating block 31, pump 32 and control means therefor mounted in a housing 33 which itself is mounted on a portable stand 34 of the type common for use with intravenous supply apparatus. Housing 33 includes means to permit vertical adjustment on stand 34 which may be in the form of a screw operated friction clamp 35 or any other suitable device.

Reservoir 26 is preferably a removable and disposable plastic container, such as an intravenous bag or a rigid container, which may be prepackaged with a fixed volume of sterile fluid, for example one liter. Clearly, just as larger or smaller catheters 1 may be used in different situations, such larger and smaller catheters will require larger or smaller volumes of fluid and this too is considered to be within the scope of this invention. Appropriate fluids include sterile water, physiological saline, and the like and should be such fluids as are biocompatible and physiologically benign in the event of inadvertent rupture of the fluid lumens 21 and 22. To allow for removal and return of the fluid in the closed system, reservoir 26 includes two fittings 36 and 37 for connection of conduits 27 and 28. These fittings may be standard piercable IV bag fittings in which case conduits 27 and 28 will be provided with appropriate piercing means.

Heating block 31 is configured to removably accept and hold reservoir 26 so as to heat the fluid contained therein. Preferably heating block 31 includes a vertical slot or window 38 which permits volume indicia 39 on reservoir 26 to be viewed. Heating block 31 itself may be a simple resistance heating means or an infrared heater or any other suitable heater capable of raising the temperature of the fluid within reservoir 26 to approximately 42° C. Heating the circulation fluid to this level has been found to provide sufficient warmth within the circulation lumens to counter the cold of a cryoprobe and maintain the urethral tissues at about normal body temperature during cryogenic surgery of the prostate. Heater control means 40 allows the operator to select the desired temperature for heater block 31 and may be accessibly provided on the outside of housing 33. An over temperature shut-off is included to prevent the fluid temperature from exceeding a maximum temperature, in this embodiment 42° C. Similarly, when used for tissue warming, the heater control means 40 does not permit adjustment to a value below that of the ambient air temperature.

Downstream from heating block 31 is pump 32 which provides motive force to the fluid to maintain a constant and even flow through the system. Pump 32 is preferably a roller pump comprising a motor driven spindle having a series of rollers which progressively compress and release conduit 27 to set up a peristaltic wave in the fluid therein. Such pumps are well known in the art. Other types of pumps which provide for regulation of fluid flow may also be used. Ideally, pump 32 operates on supply conduit 27 which conducts fluid from reservoir 26 to inflow block 7 on catheter 1. Supply conduit 27 and return conduit 28, which conducts fluid from outflow block 8 back to reservoir 26, are preferably made from flexible and resilient plastic and, like reservoir 26 and catheter 1, may be disposable. Pump 32 is provided with a speed control 41 whereby the flow rate of fluid through the system may be regulated. Preferably, flow control is incremented in units from one through ten, with one being the minimum flow, ten being the maximum and each unit corresponding to a particular flow rate. An indicator 42 provides visual confirmation of the flow rate which, in the preferred embodiment for urethral use, has a maximum setting of 1.75 liters per minute. This rate converts to a maximum pressure within the system of 25 pounds per square inch (psi).

Once the desired flow rate and temperature are set, automatic control means are activated to maintain these levels. The automatic controls include monitoring sensors for supply temperature 43, return temperature 44 and flow rate 45. Supply temperature monitor 43 is preferably located between heater block 31 and pump 32 and comprises a thermal sensor that accepts and holds supply conduit 27. An indicator 46 provides visual confirmation of the temperature of the supply flow as detected by supply temperature monitor 43. Similarly, a return temperature monitor 44 is provided for return conduit 28 and a return temperature indicator 47 is included to provide visual confirmation of this temperature. Temperature monitors 43 and 44 maintain the desired supply fluid temperature by sending signals reflecting their respective detected temperatures to a main control circuit 51 within housing 33 which compares the values of the signals and regulates heating block 31 accordingly. Thus, if the return temperature is detected as too low to maintain the desired supply temperature at the value set, control circuit 51 will adjust either the temperature of heating block 31 or its frequency of operation to ensure that the supply temperature detected by supply monitor 43 is that required. In a similar manner, flow rate sensor 45 detects the rate of fluid flow in return conduit 28 and adjusts the speed of pump 32 through control circuit 51 within housing 33 to maintain the preset flow rate through the system.

In addition to the sensors and control means, pump and heater activating switches 48 and 49 are included and electrically linked through control circuit 51 to their respective units as is a low flow alarm 50. Alarm 50 may be either visual, audible or both and activates in the event flow rate drops below a preset minimum and is not returned by the automatic controls. Placing the flow rate sensor 45 on return conduit 28 allows the system to detect low flow which may occur as the result of pump failure, blockage or rupture within catheter 1 since any one of those situations will result in a reduced or absent flow in return conduit 28. An over heat or under heat alarm may also be provided to ensure that malfunctions in the heating block 31 or its related circuitry are detected before damage occurs to the tissues being treated by the system.

Figure 5:
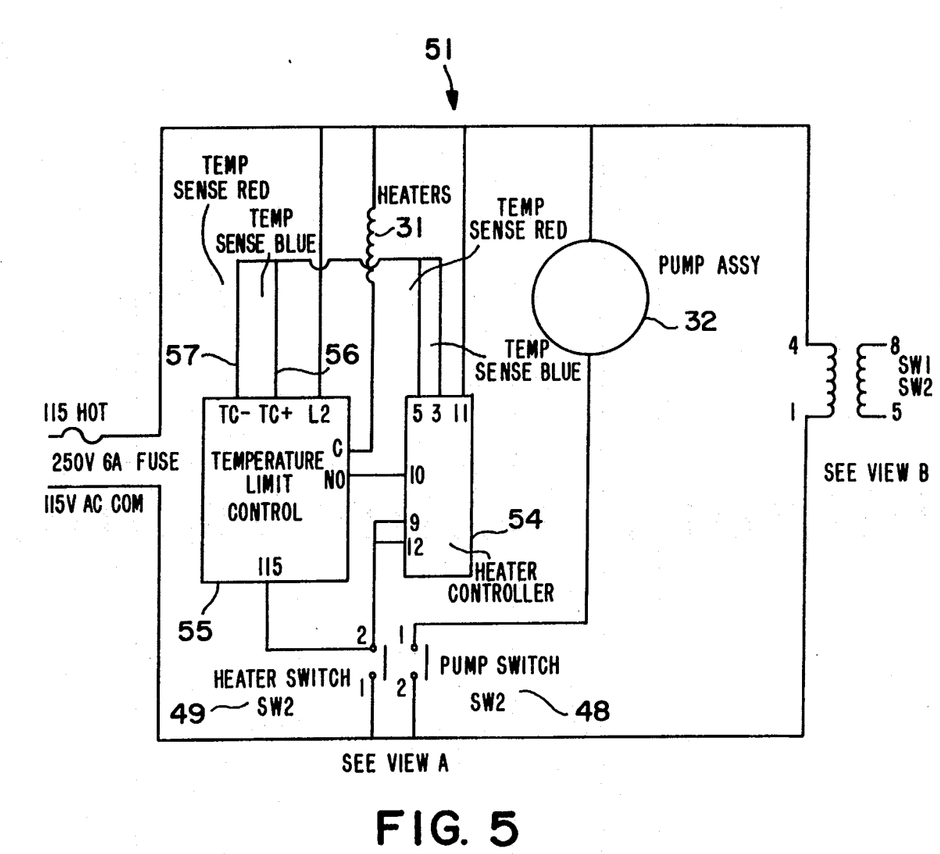
FIG. 5 is a circuit diagram of a heater and pump control circuit which may be used in the unit of FIGS. 3 and 4.
Figure 6:
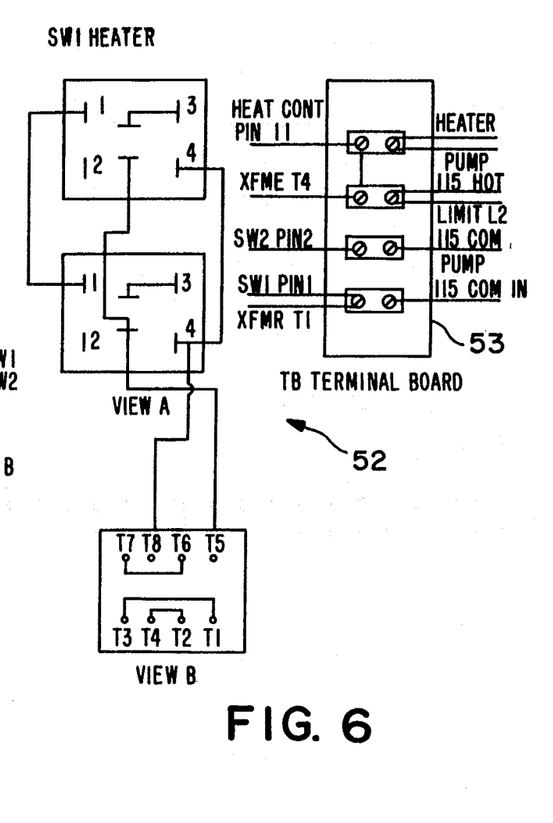
FIG. 6 is a circuit diagram for the switching portion of the circuit of FIG. 5.

Switch circuits 52 for main control 51 and for pump and heater activating switches 48 and 49 are illustrated in FIG. 6 which also shows main terminal board 53 for control unit 30. FIG. 5 illustrates one circuit of main control 51 which is principally directed to the regulation heating block 31. In this circuit, activation of heater switch 49 provides power to main heater controller 54 and to temperature limit control 55. Main heater controller 54 provides direct control to heating block 31 while temperature limit control 55 provides regulation of heater controller 54 in response to input 56 from supply temperature monitor 43 and input 57 from return temperature monitor 44. Terminal board 53 coordinates inputs and outputs between the switches, sensors, indicators, heating block 31 and pump 32.

In use, particularly for prostate surgery in combination with cryosurgical instruments generating temperatures of less than about −60° C., such as disclosed in the present assignee's copending applications, U.S. Pat. No. 07/828,732, filed Jan. 31, 1992, 07/953,279, filed Sep. 30, 1992, PCT/US91/06,814, filed Sep. 25, 1991, 07/756,287, filed Sep. 6, 1991 and PCT/US92/07,448, filed Sep. 4, 1992, control apparatus 30 is placed in the desired location in the operating room and electrically connected to an appropriate power receptacle. Fluid reservoir 26 is placed in heating block 31 and the system is activated by pressing heater switch 49 and setting heater control 40 to the desired level, typically 42° C. While the fluid in reservoir 26 is being heated, supply conduit 27 and return conduit 28 are connected to inflow and outflow blocks 7 and 8, respectively, of multi-lumen catheter 1. Supply conduit 27 is positioned in temperature monitor 43 and pump 32 and the system is then primed by activating pump 32 to express all air bubbles from the system. After priming, return conduit 28 is connected to return fitting 37 on reservoir 26 ensuring that conduit 28 is properly seated in temperature monitor 44 and flow rate monitor 45. The system is checked for leakage and the desired flow rate is selected and the temperature setting is checked. Once all desired values are achieved the surgical procedure may commence.

In the method of use the patient is anesthetized and placed in a lithotomy position and prepared for transperineal cryoablation of the prostate. A cystoscope is passed through the urethra into the bladder and a needle is inserted percutaneously into the bladder through the lower abdominal wall to facilitate insertion of a suprapubic tube. Preferably the needle is 18 gauge. Insertion of the suprapubic tube is achieved by first passing a guide wire through the needle and dilating the suprapubic track. A suprapubic catheter is then passed over the guide wire into the bladder under direct visualization with the cystoscope and the guide wire is removed. Following suprapubic insertion, a similar guide wire is passed through the cystoscope into the bladder to facilitate placement of multi-lumen catheter 1 within the patient's urethra. The cystoscope is removed, leaving the guide wire in place and multi-lumen catheter 1 is inserted into the urethra over the guide wire which is then removed. Multi-lumen catheter 1 is then connected to the rest of the system as previously described and the system is activated thereby circulating warm fluid through concentric lumens 21 and 22 to maintain the temperature of the urethra at about normal body temperature during cryoablation. Under the influence of the circulating fluid, outer sleeve 24 expands to its limit of approximately 22 French, the purpose of this expansion being to ensure good thermal contact with the inside of the urethra as opposed to dilation thereof. Once thermal stability is achieved, transperinial cryoablation of the prostate at a temperature of less than about −60° C. may proceed. Upon completion of the surgery, the circulation system is deactivated and multi-lumen catheter 1 is withdrawn. The patient may then be moved to recovery.

The herein described apparatus and method comprise an improvement over prior devices and methods in that more precise maintainence of tissue temperatures, particularly those of the urethra, is possible during cryosurgery. In addition, they increase the advantages of cryosurgery by decreasing the potential incidence of tissue damage such as urethral sloughing which is a known side effect of prostatic cryoablation under other methods as noted by R. I. Hansen and R. Donde, "Cryoprostatectomy, a Follow-up Study with Special Reference to Long-term Results", Scand. J. Urol. Nephrol. 6: 99-102, 1972. The present apparatus and method allow greater flexibility in freezing around the urethra so that the surgeon may ensure total cellular destruction of the desired area of the prostate without the added concern of damage to the urethral tissues thus permitting greater preservation of the urethral channel. In an alternative utility, the apparatus of this invention may be used to cool tissues surrounding an area where heat is applied, such as during laser ablation. In such a use heating block 31 will be replaced by a cooling block and thermal monitors 43 and 44 together with the control circuitry will be recalibrated for reduced temperatures. Also, as noted previously, further utility may be found in other areas of the body where cryosurgery or thermal surgery are conducted, for example, the gastro-intestinal tract, joint cavities, nasal passages, and the like.

The present invention has been described with reference to preferred embodiments. However, those skilled in the art will recognize that changes may be made in form and detail without departing from the spirit and the scope of the present invention.

What is claimed is:

1. A method for performing cryoablation of the prostate while maintaining the temperature of surrounding healthy tissue, including urethral tissues, at near normal body temperature, said method comprising:

inserting a multi-lumen catheter through the urethra into the bladder, allowing body liquids to drain from the bladder through a central lumen of said catheter, pumping a temperature controlled warm liquid from a source of said warm liquid countercurrently through first and second communicating concentric passageways surrounding said central lumen of said catheter and back to said source, performing transperineal cryoablation of the prostate at a temperature of less than about −60° C. until the undesired tissue is destroyed, and maintaining the flow of said warm liquid at a temperature and flow rate through said passageways sufficient to maintain the temperature of the bladder and surrounding healthy tissue at a temperature of about normal body temperature.

2. The method of claim 1 further comprising providing said source of warm liquid as a reservoir of physiological saline or sterile water within a reservoir, connecting said reservoir to said first and second communicating concentric passageways to form a closed loop circulation system and heating said liquid in said reservoir.

3. A method for performing cryoablation of the prostate while maintaining the temperature of surrounding urethral tissues comprising:

passing a multi-lumen catheter through the urethra into the bladder wherein said multi-lumen catheter comprises an elongated urethral catheter having a distal end, a proximal end and a central drainage lumen, a circulating fluid inflow block positioned concentrically on said catheter adjacent said proximal end thereof and having a fluid inflow chamber with a fluid inlet port, a circulating fluid outflow block positioned concentrically on said catheter and distally adjacent to said inflow block and having a fluid outflow chamber with a fluid outlet port, a first elongated sleeve concentric to said catheter forming a first lumen therebetween and having a proximal end extending through said outflow chamber and connected to said inflow block, and a second elongated sleeve concentric to said first sleeve forming a second lumen therebetween and having a proximal end connected to said outflow block, wherein said first sleeve terminates at a distal end proximal to said distal end of said catheter and said second sleeve terminates at a distal end between said distal end of said first sleeve and said distal end of said catheter, said distal end of said second sleeve being sealed to said catheter, said first lumen and said second lumen cooperating to form a closed loop, countercurrent flow, fluid conduit concentrically disposed along said catheter, activating a warming system to circulate warm fluid through said first and second lumens to maintain the temperature of said urethra at up to 42° C., and performing transperineal cryoablation of the prostate followed by deactivation of said warming system and removal of said multi-lumen catheter.

4. The method of claim 3 wherein the step of activating said warming system comprises connecting a first fluid conduit from a reservoir in said warming system to said inflow port and a second fluid conduit from said reservoir to said outflow port, heating a fluid in said reservoir and pumping said fluid from said reservoir through said first conduit to said first lumen, through said first lumen to said second lumen, through said second lumen to said second conduit and through said second conduit to return to said reservoir.

5. The method of claim 4 comprising providing said reservoir as a disposable container and said fluid as a sterile biocompatible fluid in said reservoir, placing said reservoir within a heating block, heating said fluid to a temperature of up to 42° C. and maintaining said temperature while said fluid is circulated through said first and second lumens.

6. The method of claim 5 wherein said sterile biocompatible fluid is sterile water or physiological saline solution.

* * * * *